(12) United States Patent
Lee

(10) Patent No.: US 11,273,321 B2
(45) Date of Patent: Mar. 15, 2022

(54) PHOTOTHERAPY APPARATUS, METHOD FOR OPERATING SAME, AND TREATMENT METHOD USING SAME

(71) Applicant: LUTRONIC CORPORATION, Goyang (KR)

(72) Inventor: Hee Chul Lee, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 0 days.

(21) Appl. No.: 16/521,932

(22) Filed: Jul. 25, 2019

(65) Prior Publication Data

US 2019/0366118 A1 Dec. 5, 2019

Related U.S. Application Data

(63) Continuation of application No. 14/651,649, filed as application No. PCT/KR2013/011399 on Dec. 10, 2013, now Pat. No. 10,363,431.

(30) Foreign Application Priority Data

Dec. 11, 2012 (KR) .......................... 10-2012-0143990

(51) Int. Cl.
*A61N 5/06* (2006.01)
*A61N 5/067* (2006.01)

(52) U.S. Cl.
CPC ............ *A61N 5/0616* (2013.01); *A61N 5/067* (2021.08); *A61N 2005/063* (2013.01);
(Continued)

(58) Field of Classification Search
CPC .......... A61N 5/0616; A61N 2005/0659; A61N 2005/0663; A61N 2005/0665; A61N 2005/067; A61N 2005/063
(Continued)

(56) References Cited

U.S. PATENT DOCUMENTS 5,943,358 A * 8/1999 Allik .................. H01S 3/08081
372/101
2004/0215175 A1* 10/2004 Feklistov .............. A61F 9/0084
606/4
(Continued)

FOREIGN PATENT DOCUMENTS

JP H11-221228 A 8/1999
KR 20-0355632 Y1 7/2004
(Continued)

OTHER PUBLICATIONS

International Search Report for PCT/KR2013/011399 filed on Dec. 10, 2013.

*Primary Examiner* — Amanda K Hulbert
*Assistant Examiner* — Natasha Patel

(57) ABSTRACT

The present invention relates to a phototherapy apparatus, to a method for operating same, and to a treatment method using same. The phototherapy apparatus includes a body including a first resonator generating a first wavelength of light, a first module connected to the body and radiating the first wavelength of light generated from the first resonator to the outside, and a second module generating a second wavelength of light using the first wavelength of light transmitted from the body and radiating the second wavelength light to the outside.

11 Claims, 8 Drawing Sheets

(a)

(b)

(52) U.S. Cl.
CPC ............ *A61N 2005/0659* (2013.01); *A61N 2005/0663* (2013.01); *A61N 2005/0665* (2013.01)

(58) Field of Classification Search
USPC .................................. 606/2–19; 607/86–94
See application file for complete search history.

(56) References Cited

U.S. PATENT DOCUMENTS

| | | | | |
|---|---|---|---|---|
| 2006/0116669 | A1* | 6/2006 | Dolleris | A61B 18/203 606/17 |
| 2006/0161142 | A1* | 7/2006 | Sierra | H01S 3/092 606/9 |
| 2006/0206173 | A1* | 9/2006 | Gertner | A61N 5/0616 607/88 |
| 2012/0215292 | A1* | 8/2012 | Gustavsson | A61N 5/0613 607/93 |
| 2013/0268031 | A1* | 10/2013 | Ko | A61N 5/0616 607/80 |

FOREIGN PATENT DOCUMENTS

| | | |
|---|---|---|
| KR | 20-0360150 Y1 | 8/2004 |
| KR | 10-0949086 B1 | 3/2010 |
| KR | 10-2011-0118039 A | 10/2011 |

* cited by examiner (a)     (b)

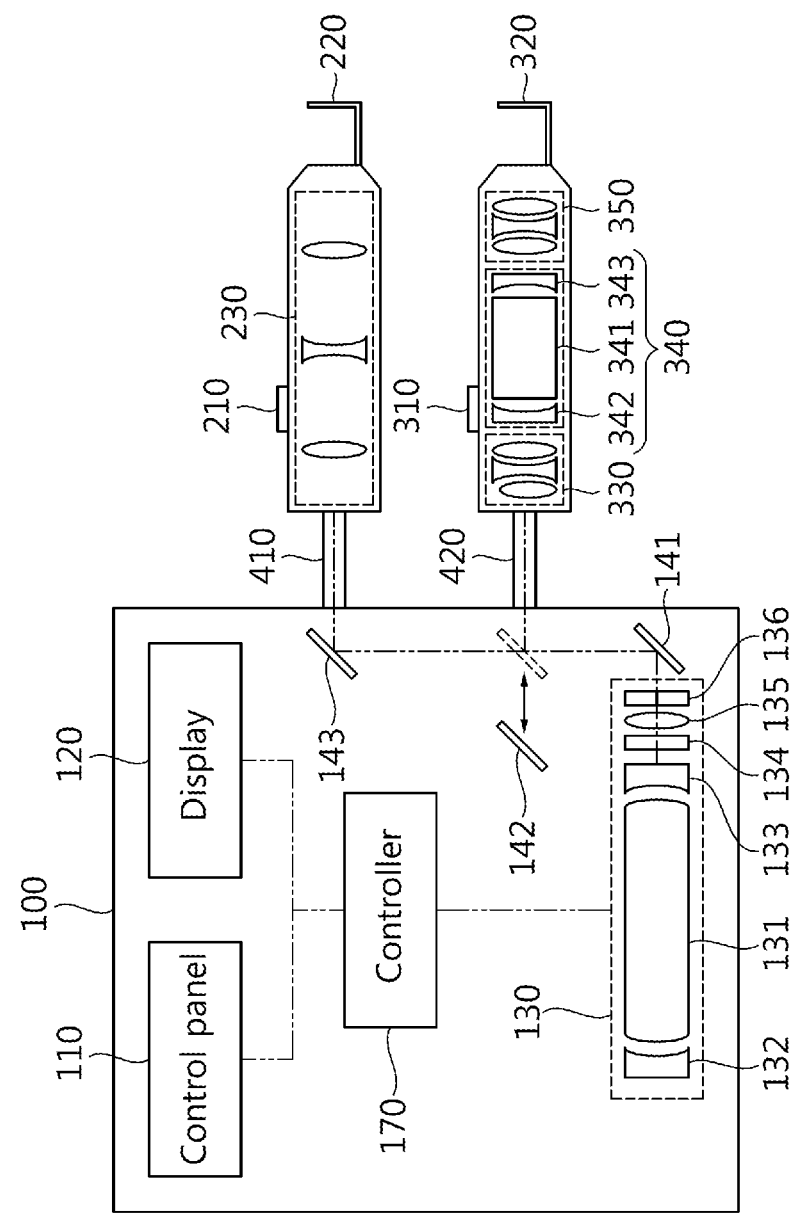

PHOTOTHERAPY APPARATUS, METHOD FOR OPERATING SAME, AND TREATMENT METHOD USING SAME

CROSS REFERENCE TO RELATED APPLICATIONS PARAGRAPH

The present application is a continuation of and claims priority to U.S. application Ser. No. 14/651,649, filed Jun. 11, 2015, which is a U.S. National Stage of PCT/KR2013/011399, filed Dec. 10, 2013, which claims priority to Korean Patent Application No. 10-2012-0143990, filed Dec. 11, 2012 in the Korean Intellectual Property Office.

BACKGROUND OF THE INVENTION

Field of the Invention

The present invention relates to a phototherapy apparatus, method for operating the same, and treatment method using the same, and more specifically, to a phototherapy apparatus radiating two wavelengths of light having different absorption characteristics and a method for operating the same and a treatment method using the same.

Related Art

Recently, human therapeutic techniques changing the state of human tissues or removing a particular tissue using light are widely being used. Accordingly, there are brisk efforts to develop light treatment apparatuses for treating various human tissues as well as human skin using various light sources such as lasers, flash lamps, or LEDs.

Such light treatment apparatuses have various absorption characteristics depending on wavelengths of light radiations, and depending on the wavelength characteristics of light illuminated, light is absorbed to various tissues including collagen, follicles, melanin, or hemoglobin. Absorbed light is converted into thermal energy in the tissue that changes the state of the tissue to thereby perform various treatments. A light treatment apparatus is disclosed in Korean Patent No. 10-0820164.

The conventional light apparatus, however, typically has a single light source for radiating light of a single wavelength, and in this case, it is difficult to implement various absorption patterns with a single band of light.

SUMMARY OF THE INVENTION

The present invention aims to provide a compact, easy-to-control phototherapy apparatus that may perform treatment using light having various wavelengths, a method for operating the same, and a treatment method using the same.

The above-described objects of the present invention may be achieved by a phototherapy apparatus comprising a body having a first resonator generating light of a first wavelength, a first module detachably provided in the body, receiving the light of the first wavelength generated from the first resonator and radiating the light of the first wavelength to an outside, and a second module detachably provided in the body, generating light of a second wavelength using the light of the first wavelength generated from the first resonator, and radiating the light of the second wavelength to the outside.

The second module may include a second resonator generating the light of the second wavelength, and the second resonator may be excited by the light of the first wavelength transferred from the body to generate the light of the second wavelength.

Here, the second resonator may include a laser dye and a pair of reflecting mirrors provided at both sides of the laser dye, and the laser dye of the second resonator may be provided to be replaceable.

The area of radiation of light radiated from each module may be various configured, and as an example, light of the second wavelength radiated through the second module may be radiated to a target position with a diameter of 4 to 20 mm.

The first module of the phototherapy apparatus may be configured to radiate light of 1064 nm or 532 nm, and the second module may be configured to radiate light of 585 nm.

On the other hand, the above-described objects of the present invention may also be achieved by a method for operating a phototherapy apparatus comprising a first operational step in which a first operator provided in a body is driven to radiate light of a first wavelength generated from the first resonator to an outside through a first module and a second operational step in which the light of the first wavelength generated from the first resonator is transferred to a second module, and the second module generates light of a second wavelength using the light of the first wavelength and radiates the light of the second wavelength to the outside.

Further, the above-described objects of the present invention may also be achieved by a treatment method comprising driving a first resonator and radiating light of a first wavelength to a tissue and generating light of a second wavelength by exciting a second resonator using the light of the first wavelength and radiating the light of the second wavelength to the tissue.

According to the present invention, a phototherapy apparatus may perform treatment in various manners using light of two different wavelengths to enhance treatment effects. The phototherapy apparatus may be configured compact and with easy-to-replace parts, thus contributing to users' convenience.

BRIEF DESCRIPTION OF THE DRAWINGS

FIG. 8 is a perspective view illustrating a phototherapy apparatus according to another embodiment of the present invention.

DESCRIPTION OF EXEMPLARY EMBODIMENTS

Hereinafter, a phototherapy apparatus, method for operating the same, and treatment method using the same according to an embodiment of the present invention are described in detail with reference to the accompanying drawings. The relationships in position between the elements in the following description are described in principle with respect to the drawings. The drawings may be simplified in structure for ease of description or may be exaggerated as necessary. Accordingly, the present invention is not limited thereto, and other various devices may be added, or some elements may be modified or omitted.

Although embodiments of phototherapy apparatuses for treating human tissues by radiating light to human skin are described as examples, the present invention is not limited thereto. The present invention may be applicable to other various treatment apparatuses that use light to treat portions other than the human skin.

Figure 1:
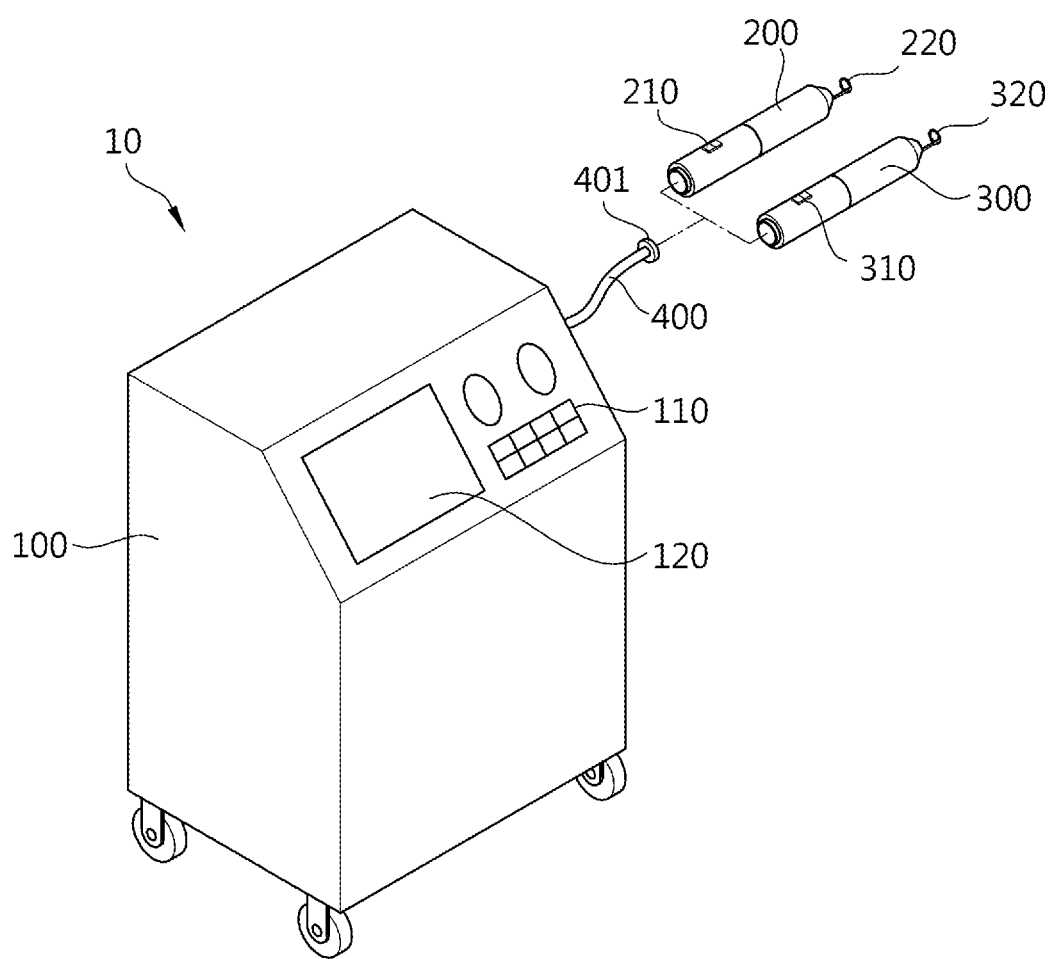
FIG. 1 is a perspective view illustrating a phototherapy apparatus according to an embodiment of the present invention.

FIG. 1 is a perspective view illustrating a phototherapy apparatus 10 according to a preferred embodiment of the present invention. As shown in FIG. 1, the phototherapy apparatus according to an embodiment of the present invention includes a body 100 and a first module 200 and a second module 300 connected with the body 100.

The body 100 includes various internal components that receive power from the outside and generate light. A control panel 110 for manipulating the drive of the phototherapy apparatus 10 and a display 120 for displaying a manipulation menu and what is operated to a user may be provided on an outer surface of the body 100.

Meanwhile, a cable 400 extends from a side of the body, and the first module and the second module may be selectively connected to a coupler 401 at an end of the cable. The coupler 401 of the cable 400 may be provided to connect with each of ends of the first module 200 and the second module 300 through screwing or other various coupling ways.

Meanwhile, the first module 200 and the second module 300 may be selectively connected to the cable 400 of the body 100 to receive light radiated from the body 100. The first module 100 and the second module 200 each include a light path along which light passes, and treatment may be performed by radiating light to the outside with the cable connected.

The first module 200 and the second module 300 may be configured as a hand piece with which the user may proceed with a procedure while changing its position with the hand piece in the user's hand. A cooling gas ejector (not shown) may be further provided in the first module 200 and the second module 300 to cool the surface of a portion being treated. Separate manipulators 210 and 220 may be respectively provided in respective outer surfaces of the first module 200 and the second module 300 for easier manipulation of light radiation and ejection of cooling gas.

The first module 200 and the second module 300 may be selectively coupled to the cable 400 as shown in FIG. 1. In this case, the cable 400 may have an optical fiber and signal line therein. Accordingly, light radiated from the body 100 may be transferred to the first module 200 or the second module 300 coupled with the cable along the optical fiber of each cable, and what is controlled through the control panel 110 of the body 100 or a signal controlled through the manipulation unit of the module connected with the cable may be delivered along a signal line of the cable.

Figure 2:
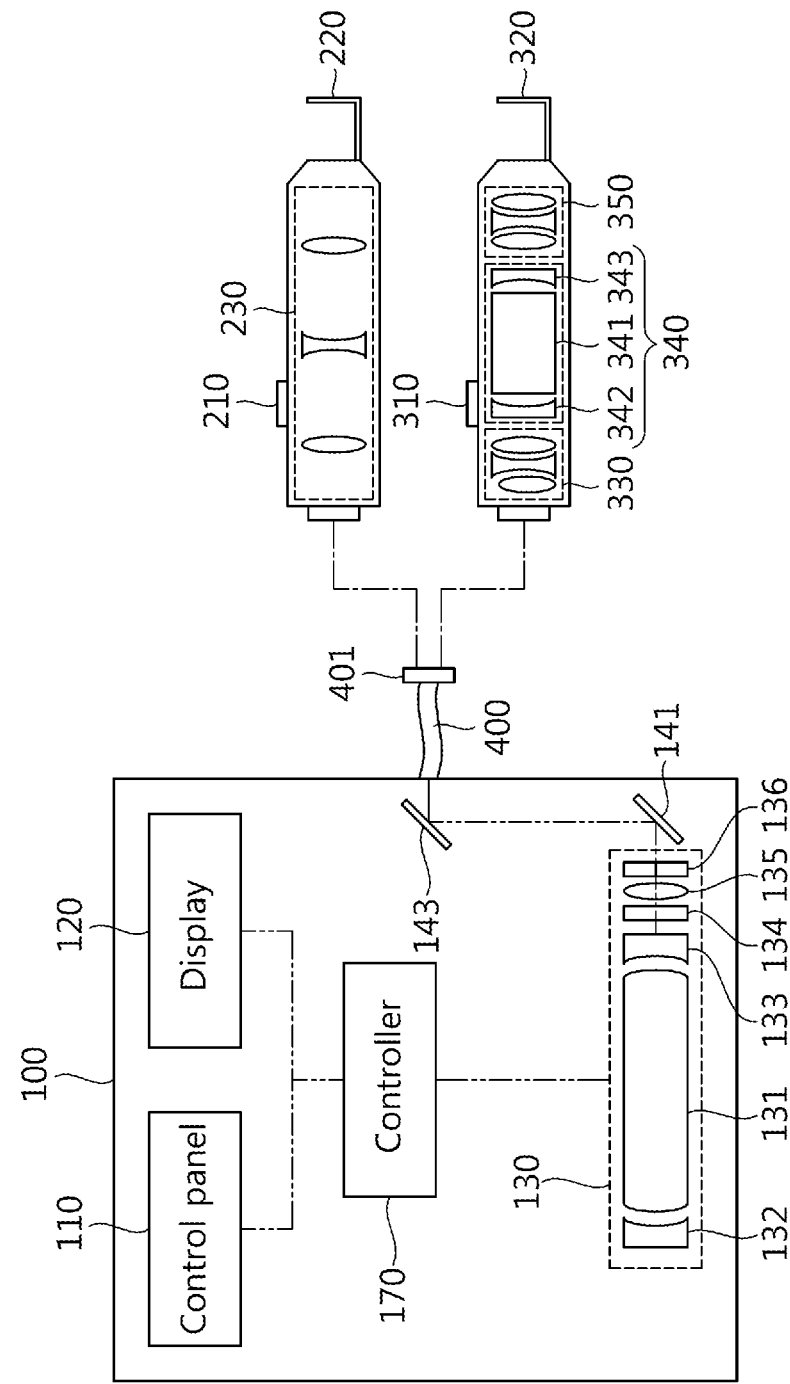
FIG. 2 is a block diagram schematically illustrating a configuration of the phototherapy apparatus of FIG. 1.

FIG. 2 is a block diagram schematically illustrating a configuration of the phototherapy apparatus of FIG. 1. Hereinafter, a configuration of a phototherapy apparatus according to an embodiment is described in further detail with reference to FIG. 2.

As shown in FIG. 2, a first resonator 130 is provided inside the body 100 to generate a first wavelength of light (hereinafter, referred to as "first light"). The first resonator 130 may include optical members, such as a laser medium 131 for radiating a laser beam and reflecting mirrors 132 and 134 provided at both sides of the laser medium 131, and a shutter 134, a filter 135, and a lens 135. Accordingly, the laser medium 131 is excited by, e.g., a flash lamp (not shown) to radiate light, and the radiated light travels back and forth between the reflecting mirrors 132 and 133 and is thus amplified, thus emitting a laser beam.

According to the present embodiment, the first resonator 130 may adopt Nd:Yag as the laser medium 131. Accordingly, the first resonator 130 may generate light having a wavelength of 1064 nm that is radiated from Nd:Yag. Further, the first resonator 130 may selectively have a KTP crystal (not shown) on a path along which the light radiated from Nd:Yag travels to generate light having a wavelength of 532 nm. Thus, the first resonator 130 according to this embodiment may selectively generate light of 1064 nm or light of 532 nm. However, the above-described type of medium of the first resonator is merely an example, and various other laser media may be used to generate light of various wavelengths.

Meanwhile, the first light generated from the first resonator 130 (in this embodiment, the light may have a wavelength of 1064 nm or 532 nm depending on what is treated) travels toward the cable along the light path formed in the body 100. Although in FIG. 2 a plurality of reflecting mirrors 141 and 143 are used to form an internal light path, this is merely an example. Other various optical devices such as an optical fiber, beam splitter, or a polarizing plate may be used to form an internal light path. The first light runs along the cable through the light path and may be delivered to the first module 200 or third module 300 provided in the coupler 401 of the cable 400.

Meanwhile, as described above, the first module 200 and the second module 300 are components that are detachable to the coupler 401 of the cable 400. Accordingly, the user may selectively couple and use the first module 200 or the second module 300 to the cable 400 depending on what is treated. However, although in this embodiment the cable extends from the body as an exemplary configuration, the first module and the second module may have their respective cables so that the cable of a corresponding module is selectively coupled to the coupler provided at an outer surface of the body.

Hereinafter, the first module and the second module are described in greater detail. First, the first module is described.

As shown in FIG. 2, the first module 200 includes a first optical device assembly 230. The first optical device assembly 230 includes at least one or more optical devices such as a plurality of lenses, filter, or shutter.

Accordingly, when the first module 200 is connected to the cable 400, the first light generated from the body is transferred through the cable, passes through the first optical device assembly 230 in the first module 200 and is then radiated to the outside through an end thereof. A first tip 220 having a predetermined length is formed at an end of the first module 200. Accordingly, the first module 200 may radiate the first light at a position spaced apart from a target position at a predetermined interval while the end of the first tip 220 contacts the target position.

The first module 200 receives light of a first wavelength generated from the first resonator 130, and without separately changing wavelength, radiates the first light itself, as treatment light, to the outside. Accordingly, according to this embodiment, it may be possible to selectively radiate light of 1064 nm or 532 nm through the first module 200.

Meanwhile, the second module 300 is also configured to be coupled to the coupler 401 of the cable 400, and may receive light generated from the first resonator 130 while connected to the coupler 401. However, the above-described first module 200 and second module 300 differ in configuration from each other in that the first module 200 receives the first light generated from the first resonator 130 of the body while the second module 300 may generate second light having a different wavelength using the first light transferred from the first resonator 130.

Figure 3:
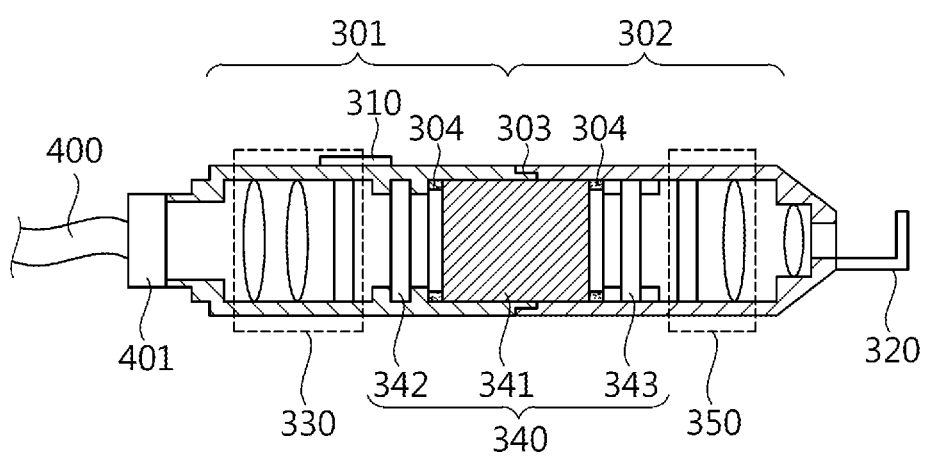
FIG. 3 is a cross-sectional view illustrating a second module of the phototherapy apparatus of FIG. 1.
Figure 4:
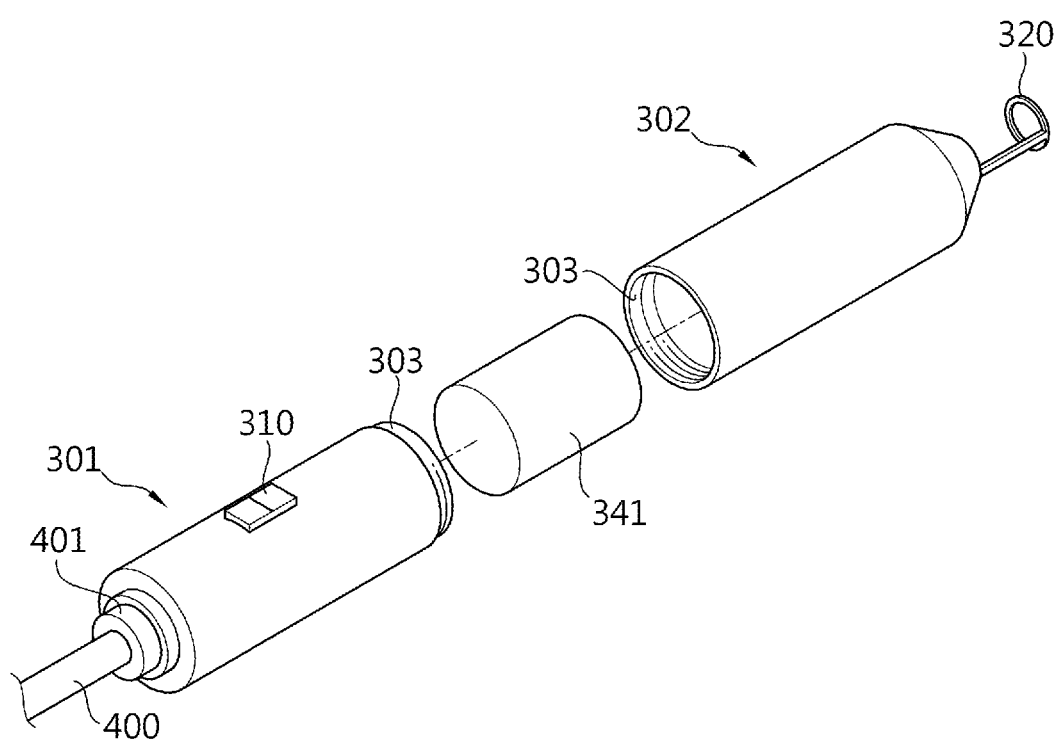
FIG. 4 is an exploded perspective view illustrating a second module of the phototherapy apparatus of FIG. 1.

Hereinafter, the second module according to this embodiment is described in greater detail with reference to FIGS. 3 and 4. FIG. 3 is a cross-sectional view illustrating the second module 300 of the phototherapy apparatus of FIG. 1, and FIG. 4 is an exploded perspective view illustrating the second module 300 of the phototherapy apparatus of FIG. 1.

As shown in FIG. 3, a second optical device assembly 330, a second resonator 340, and a third optical device assembly 350 may be provided in the second module 300. Here, the second optical device assembly 330 is provided at a position adjacent to a front end connected with the coupler 401 to allow the first light delivered through the cable 400 to be incident onto the second resonator 340. The third optical device assembly 350 is provided adjacent to an end where light is externally incident and forms a path along with light generated from the second resonator 340 travels. The second optical device assembly 330 and the third optical device assembly 350 each may include at least one or more optical devices such as a plurality of lenses, a filter, and a shutter.

Meanwhile, the second resonator 340 is provided between the second optical device assembly 330 and the third optical device assembly 350. The second resonator 340 includes a laser medium 341 and reflecting mirrors 342 and 343 disposed at both sides of the laser medium. The first light transferred through the second optical device assembly 330 may be used to generate second light.

Here, the second resonator may adopt a laser dye 341 as a laser medium to generate a dye laser beam. In this embodiment, a laser dye 341 able to generate light of 585 nm comes in use. However, other various types of laser dies may be put to use.

If the first light is incident to an inside of the second resonator 340 from the second optical device assembly 330, the first light excites the laser dye 341 to generate light of a second wavelength (in this embodiment, light of 585 nm). The light of the second wavelength generated by the laser dye 341 is resonated between the reflecting mirrors 342 and 343 provided at both sides and is then amplified. The amplified light passes through one of the reflecting mirrors and is output towards the third optical device assembly 350.

In this case, the light of the first wavelength provided from the body 100 differs in wavelength from the light of the second wavelength generated from the second resonator 340. Accordingly, the light of the first wavelength, after exciting the laser dye 341, fails to be resonated between the reflecting mirrors 342 and 343 of the second resonator 340 and thus dissipates.

Thus, the second resonator 340 may generate the second light having the second wavelength, and the second light may be radiated to the outside through the third optical device assembly 350. Here, a second tip 320 having a predetermined length is formed at an end of the second module 300, like in the first module, and the second tip 320 may be used to radiate the second light while spaced apart from the target position at a predetermined interval.

In this case, the laser dye 341 generating the light of the second wavelength is formed of a solid pigment, and when used a predetermined number of times or more, has difficulty normally outputting light. Accordingly, the present embodiment may be configured so that the laser dye 341 of the second module 300 may be replaced after a predetermined period of use.

Specifically, the second module 300 may be configured to be separated into a proximal part 301 and a distal part 302 as shown in FIGS. 3 and 4. The proximal part 301 is configured so that a side thereof may be connected with the cable 400 and has the second optical device assembly 330 and one reflecting mirror 342 of the second resonator 340 fixed therein and forms a space for accommodating part of the laser dye 341 of the second resonator 340. The distal part 302 is configured to have a second tip 320 at an end thereof and has the third optical device assembly 350 and the other reflecting mirror 343 of the second resonator 340 fixed therein and forms a space for accommodating the remainder of the laser dye 341 of the second resonator 340.

As such, the proximal part 301 and the distal part 302 of the second module 300 may be selectively coupled via a screw-shaped connecting structure 303 formed at an end, as shown in FIG. 4. Accordingly, the user may separate the proximal part 301 and the distal part 302 of the second module 300 to replace the laser dye 341 with a new laser dye and assemble them back, thus providing more convenient use.

Here, the optical devices such as the reflecting mirrors 342 and 343 constituting the second resonator 340 as well as the second and third optical device assemblies 330 and 350 are fixed to each of the proximal part 301 and distal part 302 of the second module 300. Thus, the same optical axis may be maintained by coupling the proximal part 301 with the distal part 302. A shock-absorbing member 304, such as an O-ring, is provided on an inner wall surface of the accommodating part of the proximal part and distal part forming a space for accommodating the laser dye 341. Accordingly, when the proximal part 301 and the distal part 302 are coupled, the laser dye 341 may be held at a fixed position by the O-ring, and may be thus positioned normally on the same optical axis.

As such, the phototherapy apparatus 10 according to this embodiment may enable radiation of light of two or more wavelengths in a way to exchange modules such as hand pieces using one device. Here, in configuration, the light of the first wavelength is generated in a typical manner using the solid laser provided in the body 100 while the light of the second wavelength is generated by exciting the laser dye 341 provided in the hand piece with light generated from the body 100. Accordingly, as compared with the configuration of using two solid lasers having different wavelengths, the phototherapy apparatus may be configured more compact.

Here, a dye laser that has a limited period of use as compared with a solid laser applies, but is configured to allow the user to easily replace laser dyes. Accordingly, the life span of the apparatus may be prolonged.

Meanwhile, the above-described controller 170 of the phototherapy apparatus may control various components including the first resonator 130 depending on what is manipulated while the user performs a procedure using the manipulators 210 and 310 of the first module 200 and the second module 300 or depending on operations that the user sets through the control panel 110. Accordingly, what is treated may be variously set depending on the patient's portion being treated, lesion being treated and the patient's condition, and the first light and second light may be combined to do treatment.

Figure 5:
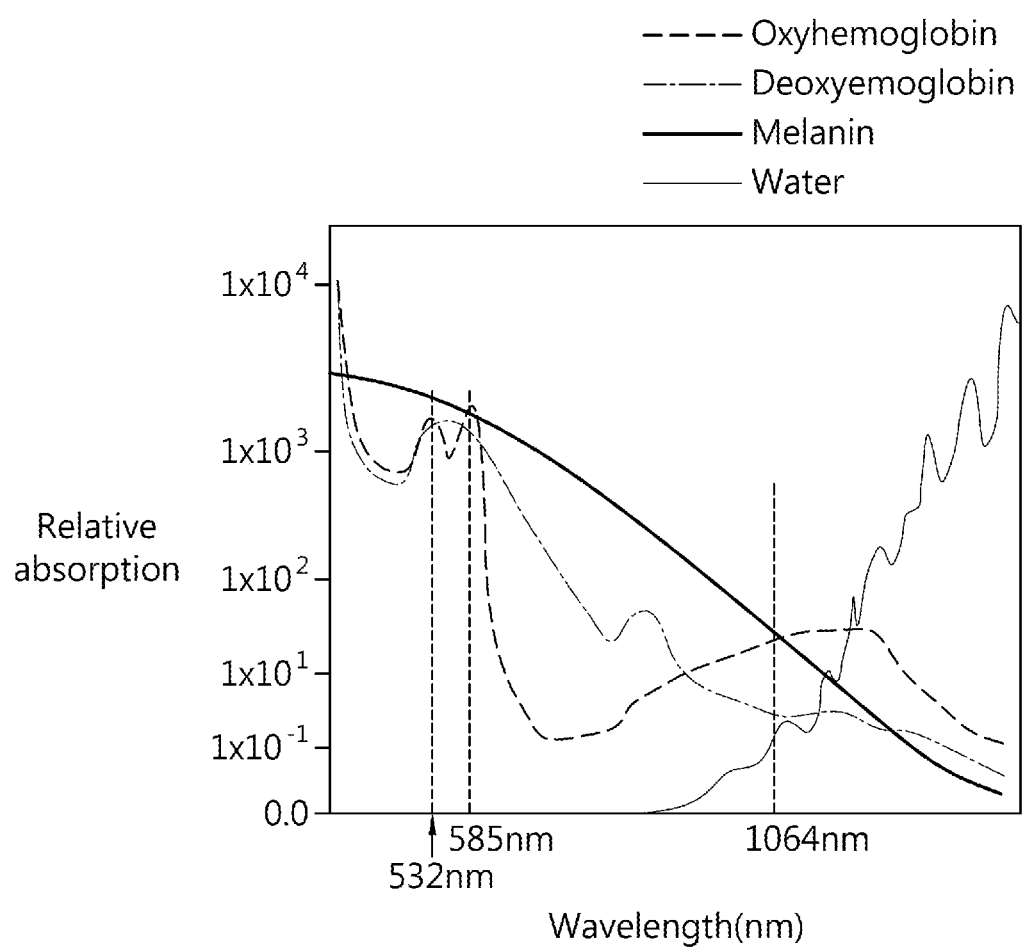
FIG. 5 is a graph illustrating absorption characteristics of a light source radiated from the phototherapy apparatus of FIG. 1.

FIG. 5 is a graph illustrating absorption characteristics of a light source radiated from the phototherapy apparatus of FIG. 1. As shown in FIG. 5, different absorption characteristics are provided depending on wavelengths of light radiated to a human tissue.

For example, light having a wavelength of 1064 nm has the characteristic of being evenly absorbed to oxyhemoglobin, deoxyhemoglobin, Melanin, and water.

Light having a wavelength of 532 nm and light having a wavelength of 585 nm have a very high absorption characteristic for oxyhemoglobin, deoxyhemoglobin, and Melanin, but a very low absorption characteristic for water.

In particular, light of 585 nm has a remarkably excellent absorption characteristic for oxyhemoglobin as compared with light of 532 nm and exhibits an effect of enhancing the health condition of the vessel passing through the area where the light is radiated. Accordingly, the light of 585 nm may penetrate up into a neighboring portion as well as the local area where the lesion has occurred to enhance the overall health condition of the vessels involving the respiration or nourishment of the tissue, thus remarkably increasing treatment effects.

Further, the light of 585 nm is excellent in absorption characteristic for oxyhemoglobin as compared with melanin and may present a noticeable effect in a special procedure such as tattoo removal as compared with light of other wavelengths.

Thus, the phototherapy apparatus according to the present embodiment may have the first module radiating light of the first wavelength and the second module radiating light of the second wavelength configured to be different from each other so as to sufficiently achieve the effects.

Specifically, the first module may be configured to transfer higher energy per unit area at the target position as compared with the second module. This may be configured in various ways by adjusting at least any one of the output of light, patterns of light pulses, and area of radiation of light radiated through the first module and the second module. In this embodiment, the first module and the second module may be configured to have different areas of radiation of light radiated through the modules to the target position, so that different levels of energy per unit area may be transferred.

Figure 6:
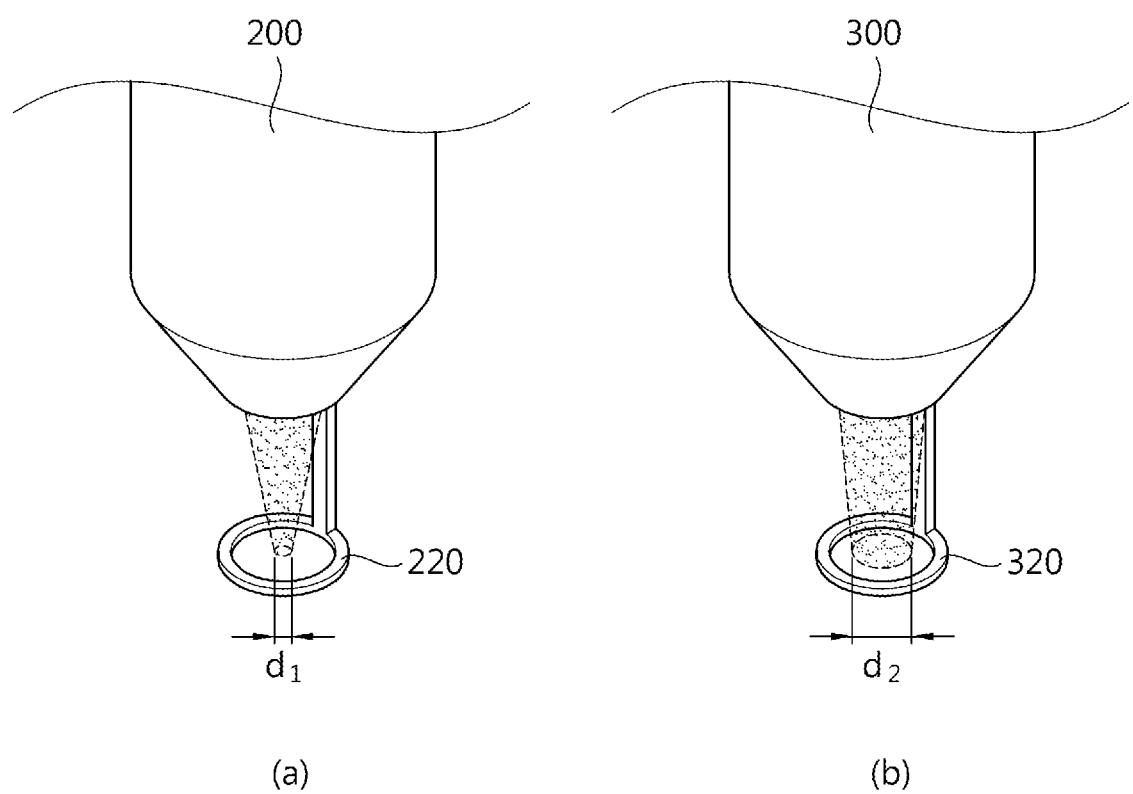
FIG. 6 is a view schematically illustrating characteristics of light radiated from a first module and a second module of the phototherapy apparatus of FIG. 1.

FIG. 6 is a view schematically illustrating characteristics of light radiated from a first module and a second module of the phototherapy apparatus of FIG. 1. As shown in FIG. 6, first light radiated through the first module 200 may be configured to be radiated to a smaller area of the target position as compared with second light radiated through the second module 300. The size of the area of radiation may be adjusted by changing the type and position of the optical device upon designing the third optical device assembly 350 provided in the second module 300 and the first optical device assembly 230 provided in the first module 200.

Here, the first light may be configured to have an area of radiation having a diameter d1 of 1 to 10 mm at the target position through the first module 200, and the second light may be configured to have an area of radiation having a diameter of d2 of 4 to 20 mm at the target position through the second module 300. Specifically, in this embodiment, the area of radiation of the first light may be configured to have a diameter of 2 mm, and the area of radiation of the second light may be configured to have a diameter of 5 mm.

Accordingly, in this embodiment, the first module 200 may transfer a higher level of energy aiming at the local area where the lesion has occurred, thus treating the lesion. In comparison, the second module 300 may radiate light to a larger area of radiation to thus radiating light up to adjacent tissues as well as the local area.

In this case, the first module may radiate light having a wavelength of 1064 nm or 532 nm to the target position aiming to the target position to thus treat the lesion such as freckles or blemishes, and the second module may evenly radiate light of 585 nm, which is lower in energy, to an adjacent position as well as the position where the lesion is present, thus enhancing the condition of vessels in charge of the nourishment and respiration of the tissue. Therefore, as compared with the conventional treatment method, the present method may effectively treat lesions and enable quick recovery.

As such, according to the present invention, there is provided a phototherapy apparatus that may radiate at least two or more different wavelengths of light, wherein light of a wavelength is used for treating a local area and light of another wavelength is used for treating a broader area. Accordingly, diverse, effective treatments may be possible, and time required for a procedure may be greatly shortened.

However, the applicable examples are merely examples for describing the present invention, and the present invention is not limited thereto. Further, the first module and the second module may be configured so that at least one or more of the internal optical devices of each module may be movable so as to adjust the area where light is radiated at the target position, and various light radiation characteristics may be configured in other various ways.

Figure 7:
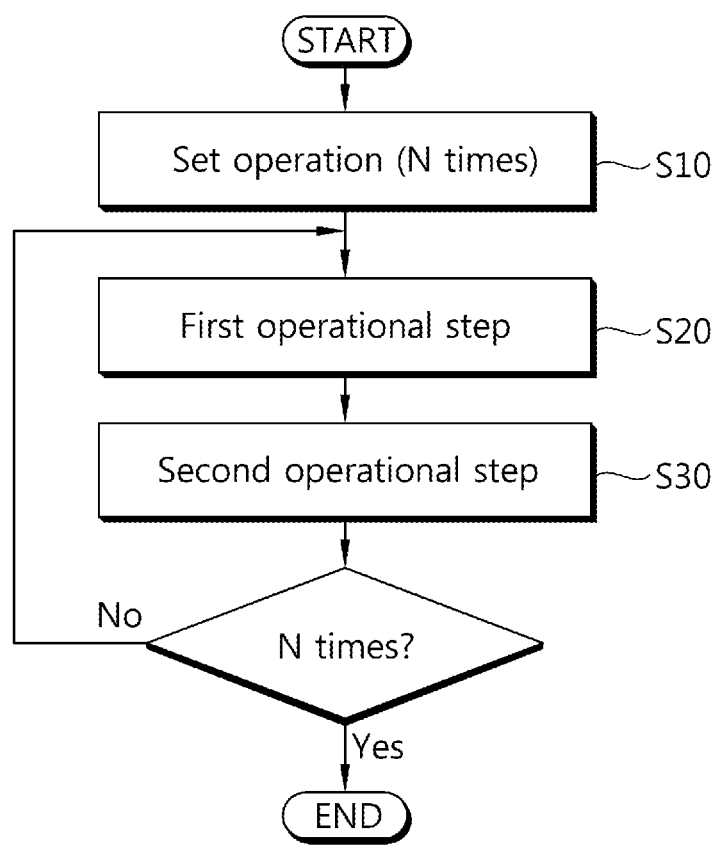
FIG. 7 is a flowchart illustrating a method for operating the phototherapy apparatus of FIG. 1.

Hereinafter, a method for operating a phototherapy apparatus and a treatment method using the same according to an embodiment of the present invention are described in detail with reference to FIG. 7. FIG. 7 is a flowchart illustrating a method for operating the phototherapy apparatus of FIG. 1.

First, the user may proceed with the step S10 of setting an operation of the phototherapy apparatus. The user may specifically set the drive of each operational step using the control panel 110, or one of the operations previously stored in a memory may be selected.

This step typically corresponds to a step for, after diagnosing the patient's lesion, treating the lesion. Accordingly, as in this embodiment, in case the first module is configured to radiate light of 532 nm and light of 1064 nm, the wavelength of light radiated through the first module 200 may be set considering the lesion of the patient in this step. Further, specific parameters of light radiated and the number (N) of times of radiation may be set using the first module 200 and the second module 300.

As an example in the present applicable example, light of 1064 nm is set to be radiated through the first module 200 to treat freckles and erythema in the skin, and settings have been made to perform three sets of treatment using the first module 200 and three sets of transmission using the second module 300 (N=3). However, this is merely an example, and what is treated may be variously set depending on the patient's lesions.

If the operation of the phototherapy apparatus is set, a first operational step proceeds (S20). The first operational step may include the step of locating the first module 200 to the target position while the first module 200 is connected to the cable and the step of radiating first light to the target position.

Here, the first operational step is performed in such a manner as treats the lesion at the position by radiating the first light of a higher output through the first module to a smaller area as described above. Accordingly, the step of locating the first module allows the freckle or erythema being treated to be positioned at the center of the first tip. The step of radiating the first light radiates the first light to the position during a predetermined time using the manipulator of the first module. In this case, the first light has a wavelength of 1064 nm and is radiated to an area having a diameter of 2 mm or less or more where the freckle or erythema is located. However, this is merely an example, and the area of radiation where the first light is radiated may be configured to be different depending on procedures and portions being subjected to procedures.

Meanwhile, in the first operational step, the first light may be repeatedly radiated in the same way to a plurality of positions showing similar lesions. Accordingly, after radiating the first light to the predetermined position, the first module is relocated to a position where a similar lesion occurs, and then the first light is radiated thereto. In such a manner, the step may be performed a plurality of numbers of times.

If the first operational step is terminated in such a way, a second operational step may be performed (S30). The second operational step may include the step of locating the second module to the target position while the second module is connected to the cable after disconnecting the first module from the cable and the step of radiating second light to the target position.

Here, the second operational step is performed in such a manner as treats a position adjacent to a lesion as well as the position wherein the lesion occurs by radiating the second light of a relatively lower output through the second module to a larger area as described above. In the step of locating the second module, thus, the second module may be located to not only the position where the freckle or erythema being treated is present but also the position adjacent thereto. The step of radiating the second light radiates the second light to the position during a predetermined time using the manipulator of the second module. In this case, the second light has a wavelength of 585 nm and is radiated to an area having a diameter of 5 mm or less or more.

In the second operational step, the second light may be repeatedly radiated in the same manner to a plurality of positions that belong to the area being treated. However, while in the first operational step, the first module is fixed at a particular position, and after the first light is radiated and then the light radiation is terminated, the first module is relocated and light radiation is resumed, the second light, unlike the first light, is radiated to transfer lower energy per unit area. Thus, light may be radiated to various positions while the position is changed, with the second light radiated. Accordingly, the time of the radiation of the second light (the time during which laser pulses are repeatedly provided) in the second operational step may be set to be longer than the time of the radiation of the first light in the first operational step.

The first operational step and the second operational step each may be performed once depending on what is treated, or in case the settings are made to repeat each step three times, the first operational step and the second operational step each may be repeated twice more and may be then terminated.

In such case, light of 1064 nm that is effective for treatment of freckles and erythema may be used to treat the local area, and light of 585 having a higher absorption for hemoglobin and melanin may be used to make up for treatment of freckles and erythema, thus allowing for increased treatment effects. Further, energy may be delivered even to an adjacent portion using light of 585 nm, mitigating pigmentation and making better the condition of the vessels in the portion being treated. Accordingly, the effect of treating the lesion and recovery mechanism may be significantly enhanced.

However, although in the above-described operational methods light of 1064 nm has been radiated from the first module to treat freckles and erythema, light of 532 nm may also be radiated from the first module to remove blemishes from the skin and make skin tone brighter. Such procedure may be performed by setting a wavelength of light radiated from the first module in the step S10 of determining the operation, the number of times in which the first operational step and the second operational step are performed and a pattern, and each operational step proceeds in a similar way to those described above and thus no detailed description thereof is given. However, in such case, the effect of treatment and recovery mechanism in removing blemishes and making skin tone brighter may be remarkably enhanced, and the time of treatment is greatly reduced.

As described above, the phototherapy apparatus according to the present invention is configured to radiate light of two different wavelengths to enable treatment of various lesions and to provide the optimal energy to each lesion, thus enhancing the effect of treatment.

Here, the phototherapy apparatus forms light of one of the two wavelengths using a dye laser and thus is configured more compact and is configured so that the laser dye may be replaced, addressing the lifespan issue that is a shortcoming of dye lasers.

Although in this embodiment, an Nd:Yag laser and a dye laser are used so that one module radiates light of 1064 nm or light of 532 nm and the other radiates light of 585 nm, this is merely an example, and various laser gain media may be utilized to radiate various wavelengths of light.

Further, although not specifically described above in connection with the embodiments, the phototherapy apparatus is configured so that the first module and the second module are selectively coupled with the cable. Accordingly, the type of the module connected may be displayed through the display of the phototherapy apparatus, or when a module of a different type than that in a set mode is connected, an error may be notified or an operation for preventing the transfer of laser beams may be performed in an additional configuration.

Further, although the first module and the second module are selectively connected to the cable of the body as illustrated, this is merely an example, and the design may be modified in various ways. For example, as shown in FIG. 8, the first module and the second module may be configured to be connected to the body via separate cables, respectively. In such case, a first light path along which light is transferred from the first resonator to the first module and a second light path along which light is transferred from the first resonator to the second module may be separately provided in the body, which function as path changer that allows some optical members (e.g., the reflecting mirror 142) therein to be selectively moved to selectively change the path along which the first light travels. The present invention may be modified in other various manners.

What is claimed is:

1. A treatment method using a phototherapy apparatus, comprising:
radiating a first light of a first wavelength to a plurality of first areas where a lesion to be treated is located so as to treat the lesion; and after radiating the first light of the first wavelength to the plurality of first areas, radiating a second light of a second wavelength to a plurality of second areas, each of the plurality of second areas comprising a corresponding one of the plurality of first areas, so as to improve a treatment effect by the first light, each of the plurality of second areas where the second light is radiated being larger than each of the plurality of first areas where the first light is radiated, wherein the second light of the second wavelength has a characteristic to be absorbed in oxyhemoglobin better than the first light of the first wavelength, so that a condition of a vessel passing through the plurality of second areas where the second light is radiated is enhanced in a respiration or nourishment of tissue so as to increase the treatment effect.

2. The treatment method of claim 1, wherein the lesion is one selected from a group comprising a freckle, an erythema and blemishes.

3. The treatment method of claim 1, wherein the first light is radiated to each of the plurality of first areas having a diameter of 1 to 10 mm, and the second light is radiated to each of the plurality of second areas having a diameter of 4 to 20 mm.

4. The treatment method of claim 1, wherein the second light transfers lower energy per unit radiated area than the first light.

5. The treatment method of claim 1, wherein the first wavelength is 1064 nm or 532 nm.

6. The treatment method of claim 1, wherein the second wavelength is 585 nm.

7. The treatment method of claim 1, wherein the first light of the first wavelength is generated from a first resonator of the phototherapy apparatus, and the second light of the second wavelength is generated from a second resonator which is excited by the first light of the first wavelength.

8. The treatment method of claim 7, wherein the phototherapy apparatus comprises:
 a body having the first resonator;
 a first module connected to the body, receiving the first light wavelength generated from the first resonator and radiating the first light of the first wavelength to the plurality of first areas; and
 a second module connected to the body, comprising the second resonator to generate the second light of the second wavelength using the first light of the first wavelength, and radiating the second light of the second wavelength to the plurality of second areas.

9. The treatment method of claim 8, wherein the second resonator includes a laser dye and a pair of reflecting means provided at both sides of the laser dye.

10. The treatment method of claim 8, wherein the body includes a first path along which the light of the first wavelength generated from the first resonator is transferred to the first module and a second path along which the light of the first wavelength generated from the first resonator is transferred to the second module, and further includes a path adjuster allowing the light of the first wavelength to be transferred through one of the first path and the second path.

11. The treatment method of claim 1, wherein the first light of the first wavelength is radiated to the plurality of first areas during a first time interval, and the second light of the second wavelength is radiated to the plurality of second areas during a second time interval, the second time interval is longer than the first time interval.

\* \* \* \* \*